United States Patent
Liu et al.

(10) Patent No.: US 10,213,493 B2
(45) Date of Patent: Feb. 26, 2019

(54) PROTEIN TO PROMOTE BLOOD VESSEL GROWTH AND USES THEREOF

(71) Applicant: Georgia State University Research Foundation, Atlanta, GA (US)

(72) Inventors: Zhi-Ren Liu, Marietta, GA (US); Liangwei Li, Atlanta, GA (US); Yinwei Zhang, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 14/385,041

(22) PCT Filed: Mar. 15, 2013

(86) PCT No.: PCT/US2013/031992
§ 371 (c)(1),
(2) Date: Sep. 12, 2014

(87) PCT Pub. No.: WO2013/138704
PCT Pub. Date: Sep. 19, 2013

(65) Prior Publication Data
US 2015/0374799 A1  Dec. 31, 2015

(51) Int. Cl.
| | |
|---|---|
| *A61K 35/28* | (2015.01) |
| *A61K 38/45* | (2006.01) |
| *A61K 9/00* | (2006.01) |
| *A61K 9/06* | (2006.01) |
| *A61K 45/06* | (2006.01) |

(52) U.S. Cl.
CPC ............ *A61K 38/45* (2013.01); *A61K 9/0014* (2013.01); *A61K 9/06* (2013.01); *A61K 35/28* (2013.01); *A61K 45/06* (2013.01); *C12Y 207/0104* (2013.01)

(58) Field of Classification Search
None
See application file for complete search history.

(56) References Cited

PUBLICATIONS

Ignacak et al., "Amino-acid composition of pyruvate kinase M2 isozyme variants from rat liver and Morris hepatoma 7777", Acta Biochimica Polonica, 1998, 45(2):775-780.*
Li et al., "Pyruvate Kinase M2 in Blood Circulation Facilitates Tumor Growth by Promoting Angiogenesis", The Journal of Biological Chemistry, 2014, vol. 289, No. 37, pp. 25812-25821.*
Zhang et al., "PKM2 released by neutrophils at wound site facilitates early wound healing by promoting angiogenesis", Wound Repair and Regeneration, Mar. 2016, 24(2):328-336. DOI: 10.1111/wrr.12411.*
Gupta et al., "Human pyruvate kinase M2: A multifunctional protein", Protein Science 2010, vol. 19, pp. 2031-2044.*

* cited by examiner

*Primary Examiner* — Suzanne M Noakes
(74) *Attorney, Agent, or Firm* — Lewis Brisbois Bisgaard & Smith LLP (57) ABSTRACT

A method for stimulating angiogenesis in a tissue of a mammal comprising contacting tissue with a protein substantially similar to pyruvate kinase M2.

13 Claims, 6 Drawing Sheets
Specification includes a Sequence Listing.

FIG. 6

SEQUENCE LISTING

<160> NUMBER OF SEQ ID NOS: 3

<210> SEQ ID NO 1
<211> LENGTH: 531
<212> TYPE: PRT
<213> ORGANISM: Human

<400> SEQUENCE: 1

```
Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
```

```
                    275                 280                 285
Gly Ile Met Val Ala Arg Gly Asp Leu Gly Ile Glu Ile Pro Ala Glu
    290                 295                 300
Lys Val Phe Leu Ala Gln Lys Met Met Ile Gly Arg Cys Asn Arg Ala
305                 310                 315                 320
Gly Lys Pro Val Ile Cys Ala Thr Gln Met Leu Glu Ser Met Ile Lys
                325                 330                 335
Lys Pro Arg Pro Thr Arg Ala Glu Gly Ser Asp Val Ala Asn Ala Val
            340                 345                 350
Leu Asp Gly Ala Asp Cys Ile Met Leu Ser Gly Glu Thr Ala Lys Gly
        355                 360                 365
Asp Tyr Pro Leu Glu Ala Val Arg Met Gln His Leu Ile Ala Arg Glu
    370                 375                 380
Ala Glu Ala Ala Ile Tyr His Leu Gln Leu Phe Glu Glu Leu Arg Arg
385                 390                 395                 400
Leu Ala Pro Ile Thr Ser Asp Pro Thr Glu Ala Thr Ala Val Gly Ala
                405                 410                 415
Val Glu Ala Ser Phe Lys Cys Cys Ser Gly Ala Ile Ile Val Leu Thr
            420                 425                 430
Lys Ser Gly Arg Ser Ala His Gln Val Ala Arg Tyr Arg Pro Arg Ala
        435                 440                 445
Pro Ile Ile Ala Val Thr Arg Asn Pro Gln Thr Ala Arg Gln Ala His
    450                 455                 460
Leu Tyr Arg Gly Ile Phe Pro Val Leu Cys Lys Asp Pro Val Gln Glu
465                 470                 475                 480
Ala Trp Ala Glu Asp Val Asp Leu Arg Val Asn Phe Ala Met Asn Val
                485                 490                 495
Gly Lys Ala Arg Gly Phe Phe Lys Lys Gly Asp Val Val Ile Val Leu
            500                 505                 510
Thr Gly Trp Arg Pro Gly Ser Gly Phe Thr Asn Thr Met Arg Val Val
        515                 520                 525
Pro Val Pro
    530

<210> SEQ ID NO 2
<211> LENGTH: 531
<212> TYPE: PRT
<213> ORGANISM: Artificial Sequence
<220> FEATURE:
<223> OTHER INFORMATION: R399E Mutant

<400> SEQUENCE: 2

Met Ser Lys Pro His Ser Glu Ala Gly Thr Ala Phe Ile Gln Thr Gln
1               5                   10                  15
Gln Leu His Ala Ala Met Ala Asp Thr Phe Leu Glu His Met Cys Arg
            20                  25                  30
Leu Asp Ile Asp Ser Pro Pro Ile Thr Ala Arg Asn Thr Gly Ile Ile
        35                  40                  45
Cys Thr Ile Gly Pro Ala Ser Arg Ser Val Glu Thr Leu Lys Glu Met
    50                  55                  60
Ile Lys Ser Gly Met Asn Val Ala Arg Leu Asn Phe Ser His Gly Thr
65                  70                  75                  80
His Glu Tyr His Ala Glu Thr Ile Lys Asn Val Arg Thr Ala Thr Glu
                85                  90                  95
Ser Phe Ala Ser Asp Pro Ile Leu Tyr Arg Pro Val Ala Val Ala Leu
```

```
                100               105               110
Asp Thr Lys Gly Pro Glu Ile Arg Thr Gly Leu Ile Lys Gly Ser Gly
            115                 120                 125

Thr Ala Glu Val Glu Leu Lys Lys Gly Ala Thr Leu Lys Ile Thr Leu
            130                 135             140

Asp Asn Ala Tyr Met Glu Lys Cys Asp Glu Asn Ile Leu Trp Leu Asp
145                     150                 155                 160

Tyr Lys Asn Ile Cys Lys Val Val Glu Val Gly Ser Lys Ile Tyr Val
                    165                 170                 175

Asp Asp Gly Leu Ile Ser Leu Gln Val Lys Gln Lys Gly Ala Asp Phe
            180                 185                 190

Leu Val Thr Glu Val Glu Asn Gly Ser Leu Gly Ser Lys Lys Gly
            195                 200                 205

Val Asn Leu Pro Gly Ala Ala Val Asp Leu Pro Ala Val Ser Glu Lys
            210                 215                 220

Asp Ile Gln Asp Leu Lys Phe Gly Val Glu Gln Asp Val Asp Met Val
225                     230                 235                 240

Phe Ala Ser Phe Ile Arg Lys Ala Ser Asp Val His Glu Val Arg Lys
                    245                 250                 255

Val Leu Gly Glu Lys Gly Lys Asn Ile Lys Ile Ser Lys Ile Glu
            260                 265                 270

Asn His Glu Gly Val Arg Arg Phe Asp Glu Ile Leu Glu Ala Ser Asp
            275                 280                 285

Gly Ile Met Val Ala Arg Gly Asp Leu Gly Ile Glu Ile Pro Ala Glu
            290                 295                 300

Lys Val Phe Leu Ala Gln Lys Met Met Ile Gly Arg Cys Asn Arg Ala
305                     310                 315                 320

Gly Lys Pro Val Ile Cys Ala Thr Gln Met Leu Glu Ser Met Ile Lys
                    325                 330                 335

Lys Pro Arg Pro Thr Arg Ala Glu Gly Ser Asp Val Ala Asn Ala Val
                    340                 345                 350

Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
            370                 375                 380

Ala Glu Ala Ala Ile Tyr His Leu Gln Leu Phe Glu Glu Leu Glu Arg
385                     390                 395                 400

Leu Ala Pro Ile Thr Ser Asp Pro Thr Glu Ala Thr Ala Val Gly Ala
                    405                 410                 415

Val Glu Ala Ser Phe Lys Cys Cys Ser Gly Ala Ile Ile Val Leu Thr
                    420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
            450                 455                 460

Leu Tyr Arg Gly Ile Phe Pro Val Leu Cys Lys Asp Pro Val Gln Glu
465                     470                 475                 480

Ala Trp Ala Glu Asp Val Asp Leu Arg Val Asn Phe Ala Met Asn Val
                    485                 490                 495

Gly Lys Ala Arg Gly Phe Phe Lys Lys Gly Asp Val Val Ile Val Leu
                    500                 505                 510

Thr Gly Trp Arg Pro Gly Ser Gly Phe Thr Asn Thr Met Arg Val Val
            515                 520                 525
```

```
Pro Val Pro
    530

<210> SEQ ID NO 3
<211> LENGTH: 531
<212> TYPE: PRT
<213> ORGANISM: Artificial Sequence
<220> FEATURE:
<223> OTHER INFORMATION: Y105E Mutant

<400> SEQUENCE: 3

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Glu Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
    210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
    290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350
```

```
Leu Asp Gly Ala Asp Cys Ile Met Leu Ser Gly Glu Thr Ala Lys Gly
        355                 360                 365
Asp Tyr Pro Leu Glu Ala Val Arg Met Gln His Leu Ile Ala Arg Glu
    370                 375                 380
Ala Glu Ala Ala Ile Tyr His Leu Gln Leu Phe Glu Glu Leu Arg Arg
385                 390                 395                 400
Leu Ala Pro Ile Thr Ser Asp Pro Thr Glu Ala Thr Ala Val Gly Ala
                405                 410                 415
Val Glu Ala Ser Phe Lys Cys Cys Ser Gly Ala Ile Ile Val Leu Thr
                420                 425                 430
Lys Ser Gly Arg Ser Ala His Gln Val Ala Arg Tyr Arg Pro Arg Ala
            435                 440                 445
Pro Ile Ile Ala Val Thr Arg Asn Pro Gln Thr Ala Arg Gln Ala His
    450                 455                 460
Leu Tyr Arg Gly Ile Phe Pro Val Leu Cys Lys Asp Pro Val Gln Glu
465                 470                 475                 480
Ala Trp Ala Glu Asp Val Asp Leu Arg Val Asn Phe Ala Met Asn Val
                485                 490                 495
Gly Lys Ala Arg Gly Phe Phe Lys Lys Gly Asp Val Val Ile Val Leu
            500                 505                 510
Thr Gly Trp Arg Pro Gly Ser Gly Phe Thr Asn Thr Met Arg Val Val
        515                 520                 525
Pro Val Pro
    530
```

PROTEIN TO PROMOTE BLOOD VESSEL GROWTH AND USES THEREOF

STATEMENT REGARDING FEDERALLY SPONSORED RESEARCH OR DEVELOPMENT

This invention was made with Government Support under Agreement CA118113 by the National Institutes of Health. The Government has certain rights in the invention.

PRIOR RELATED APPLICATION DATA

This application claims priority to U.S. Provisional Patent Application Ser. No. 61/611,555, filed Mar. 15, 2012, which is incorporated by reference in its entirety.

BACKGROUND

The disclosure relates to methods for promoting angiogenesis, including vascularizing an avascular site, or extending or enhancing existing vasculature.

BRIEF DESCRIPTION OF THE DRAWINGS

The detailed description particularly refers to the accompanying figures in which.

DEFINITIONS

The following definitions are provided to facilitate understanding of certain terms used throughout this specification.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, by way of example only, an alpha.-carbon that is bound to a hydrogen, a carboxyl group, an amino group, and an R group. Such analogs may have modified R groups (by way of example, norleucine) or may have modified peptide backbones, while still retaining the same basic chemical structure as a naturally occurring amino acid. Non-limiting examples of amino acid analogs include homoserine, norleucine, methionine sulfoxide, methionine methyl sulfonium.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. By way of example, an agent or a compound being administered includes, but is not limited to, a natural amino acid polypeptide, non-natural amino acid polypeptide, modified natural amino acid polypeptide, or modified non-amino acid polypeptide.

Compositions containing such natural amino acid polypeptides, non-natural amino acid polypeptides, modified natural amino acid polypeptides, or modified non-natural amino acid polypeptides can be administered for prophylactic, enhancing, and/or therapeutic treatments.

An appropriate "effective" amount in any individual case may be determined using techniques, such as a dose escalation study.

The term "nucleic acid sequence" as used herein, refers to the order and identity of the nucleotides comprising a nucleic acid.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "pharmaceutically acceptable", as used herein, refers to a material, including but not limited to, a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "prophylactically effective amount," as used herein, refers that amount of a composition containing at least one non-natural amino acid polypeptide or at least one modified non-natural amino acid polypeptide prophylactically applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The phrase "substantially similar," in the context of two nucleic acids or polypeptides, refers to two or more sequences or subsequences that have at least 75%, or at least 85%, or at least 90%, 95% or higher or any integral value therebetween nucleotide or amino acid residue identity, when compared and aligned for maximum correspondence, as measured using a sequence comparison algorithm such as those described below for example, or by visual inspection. A substantial identity exists over a region of the sequences that is at least about 10, or about 20, or about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

The term "therapeutically effective amount," as used herein, refers to the amount of a composition containing at least one non-natural amino acid polypeptide and/or at least one modified non-natural amino acid polypeptide administered to a patient already suffering from a disease, condition or disorder, sufficient to cure or at least partially arrest, or relieve to some extent one or more of the symptoms of the disease, disorder or condition being treated. The effectiveness of such compositions depend conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial. A therapeutically effective amount of protein kinase M2 or variant thereof would include an amount that can stimulate angiogenesis.

The term "subject" as used herein includes mammals and humans.

The term "effective amount" is meant to include any amount of pyruvate kinase M2 or variant thereof that is sufficient to bring about a desired therapeutic result, especially upon administration to an animal or human subject.

The term "dosage" as used herein refers to the amount of pyruvate kinase M2 or variant thereof administered to an animal or human. Suitable dosage units for use in the methods of the present invention range from mg/kg body weight of the recipient subject to mg/kg. The therapeutic agent may be delivered to the recipient as a bolus or by a sustained (continuous or intermittent) delivery.

DETAILED DESCRIPTION

The angiogenic activity and/or endothelial cell proliferative or migration potential of a pyruvate kinase M2, or a protein substantially similar to pyruvate kinase, can be assessed by assays and methodology. The pyruvate kinase protein can be any vertebrate or mammalian pyruvate kinase, and may be a native pyruvate kinase, or a recombinant or other synthetic protein. The amino acid sequence for human pyruvate kinase is for instance provided by GenBank Accession No. MP0011193727 pyruvate kinase. The amino acid sequence identity of pyruvate kinase for example is highly conserved between species with human having 98% amino acid sequence identity with mouse, hamster and rat. The amino acid sequence for human pyruvate kinase is disclosed herein. In one specific embodiment, angiogenic active pyruvate kinase protein is a dimer, that is, the subtype M2. A broad range of proteins substantially similar to pyruvate kinase M2 are useful with specific embodiments.

An animal from which native pyruvate kinase protein is purified can for instance be a member of the bovine, ovine, porcine, equine, canine, feline, primate, rodent or other mammalian family. In at least some forms, the pyruvate kinase protein will be a human pyruvate kinase protein purified from bacterial production.

A recombinant pyruvate kinase protein can have an identical amino acid sequence to the native pyruvate kinase or one or more amino acid differences compared to the native protein. The amino acid changes can comprise the addition, deletion and/or substitution of one or more amino acids. Inversion of amino acids and other mutational changes that result in modification of the native pyruvate kinase protein sequence are also encompassed. Moreover, a recombinant protein can comprise an amino acid or amino acids not encoded by the genetic code.

The substitution of an amino acid can be a conservative or non-conservative substitution. The term conservative amino acid substitution is to be taken in the normally accepted sense of replacing an amino acid residue with another amino acid having similar properties which substantially does not adversely affect the angiogenic and/or wound healing activity of the pyruvate kinase protein. For example, a conservative amino acid substitution can involve substitution of a basic amino acid such as arginine with another basic amino acid such as lysine. Likewise, for instance a cysteine residue can be replaced with serine, or a non-polar amino acid may be substituted with another non-polar amino acid such as alanine Amino acids amenable to substitution or deletion in a pyruvate kinase protein amino acid sequence may be determined by comparison of the sequence with closely related pyruvate kinase proteins to identify non-conserved amino acids and by routine trial and experimentation well within the skill of the addressee. A modified recombinant pyruvate kinase protein can be provided by introducing nucleotide change(s) in nucleic acid sequence encoding the native protein such that the desired amino acid changes are achieved upon expression of the nucleic acid in a host cell.

A recombinant or other synthetic pyruvate kinase protein useful in a method embodied by the invention will have amino acid sequence identity with the native pyruvate kinase of about 60% or greater, and more usually at least about 70%, 80%, 90%, 95%, 98% or greater, or 100%, and all sequence homologies and ranges thereof within those enumerated above are expressly encompassed. Sequence identity between amino acid sequences is determined by comparing amino acids at each position in the sequences when optimally aligned for the purpose of comparison. The sequences are considered identical at a position if the amino acids at that position are the same. A gap, that is a position in an alignment where an amino acid residue is present in one sequence but not the other is regarded as a position with non-identical residues. Alignment of sequences may be performed using any suitable program or algorithm. Computer assisted sequence alignment can be conveniently performed using standard software programs.

The pyruvate kinase protein can also be chemically synthesized. The provision and use of fusion proteins incorporating a pyruvate kinase protein as described herein is also expressly encompassed by the invention. Nucleic acid encoding a fusion protein can be provided by joining separate DNA fragments encoding the pyruvate kinase protein and, for example, a lipophilic amino acid sequence for enhancing the lipophilic characteristics of the protein by employing blunt-ended termini and oligonucleotide linkers, digestion to provide staggered termini and ligation of cohesive ends as required.

Host cells that can be transfected for expression of recombinant pyruvate kinase proteins and fusion proteins as described herein include bacteria such as *E. coli, Bacillus* strains (eg., *B. subtilis*), *Streptomyces* and *Pseudomonas* bacterial strains, yeast such as *Sacchromyces* and *Pichia*, insect cells, avian cells and mammalian cells such as Chinese Hamster Ovary cells (CHO), COS, HeLa, HaRas, W138, SW480, and NIH3T3 cells. The host cells are cultured in a suitable culture medium under conditions for expression of the introduced nucleic acid (typically in an appropriate expression vector) prior to purification of the expressed product from the host cells, and/or supernatants as required using standard purification techniques.

Pyruvate kinase proteins as described herein can also be modified by coupling one or more proteinaceous or non-proteinaceous moieties to the protein to improve solubility, lipophilic characteristics, stability, biological half-life, or for instance to act as a label for subsequent detection or the like. Modifications can also result from post-translational or post-synthesis modification such as by the attachment of carbohydrate moieties, or chemical reaction(s) resulting in structural modification(s) (e.g., the alkylation or acetylation of one or more amino acid residues or other changes involving the formation of chemical bonds). For example, the pyruvate kinase protein can have one or more modifications selected from the group consisting of methylation, phosphorylation, oxidation of tyrosine and/or tryptophan residues, glycosylation, and S-methylcysteine covalent attachment.

The pyruvate kinase protein can be of a size with a range of deviating from the complete protein. However, the pyruvate kinase should have a length sufficient to enable a dimer formation.

C-terminal and N-terminal extensions of native pyruvate kinase proteins are involved in stabilization of quaternary structure and the generation of aggregates of the protein. Thus, pyruvate kinases lacking such C-terminal and N-terminal extensions forms aggregates poorly. Pyruvate kinases form large aggregates. Electrostatic interactions between pyruvate kinase proteins are also involved in pyruvate kinase aggregate formation, and ionization of histidine residues below a pH of 7 can disrupt the aggregates. Typically, the pyruvate kinase protein used in a method embodied by the invention will be in dimeric form.

The intact and truncated forms of a pyruvate kinase protein useful in embodiments of the invention may be subjected to post translational modifications not limited to acetylation, methylation, ethylation, phosphorylation, oxidation and glycosylation modifications in the native pyruvate kinase protein. Suitable conditions for alkaline phosphatase activity include suitable zinc, magnesium or calcium containing buffers.

Partially hydrolysed forms of pyruvate kinase proteins can be purified for use in embodiments of the invention by any suitable purification technique including, e.g., filtration and chromatography protocols.

Tissue sites and wounds that may be treated in accordance with the invention include acute and chronic wounds, burns including burns arising from exposure to ionizing radiation, chemical wounds, surgical wounds, oral wounds, skin and muscle trauma, open skin wounds, diabetic skin sores including diabetic foot ulcers, diabetic naturopathic foot ulcers, ischemic tissue including ischemic naturopathic foot ulcers, venous stasis ulcers, pressure sores, and hypoxic tissue. Examples of ischemic and hypoxic tissues include ischemic heart tissue and hypoxic tissues associated with stroke. Conditions in which the wound healing process may be promoted by the administration of the pyruvate kinase protein include in circumstances of delayed wound healing in which healing is impaired or prevented by for example, tissue hypoxia, repeated trauma, or systemic causes such as diabetes and vascular disease. Examples of endothelial cell types that may be induced to proliferate and/or migrate by pyruvate kinase proteins in accordance with the invention include human umbilical vein endothelial cells, human microvascular endothelial cells, and aorta endothelial cells.

The pyruvate kinase protein can be administered to a subject so to stabilize stems cells and tissue cultures within the subject. By administrating the protein, the culture or cells may undergo angiogenesis.

In one specific embodiment, stem cells can be treated with a pyruvate kinase protein so to facilitate blood vessel to the transplanted stem cells, so to promote survival of the stem cells. The source of the stem cells may be adipose stromal cells, embryonic stem cells, and/or stem cells derived from bone marrow aspirate. The stem cells can be mammalian stem cells, and in various embodiments, are human stem cells. Stem cells can be applied to the site just prior to the administration of the pyruvate kinase protein, and can be mixed with stem cells for co-transplantation.

In another embodiment, tissue transplantation may be facilitated by the treatment of the transplanted tissue with protein substantially similar to pyruvate kinase or pyruvate kinase. The transplanted tissue may be treated with pyruvate kinase protein. A scaffold may be included to contain, support, or retain the pyruvate kinase protein, along with other materials, at the tissue defect site. In one example, a scaffold may contain or support stem cells to enabling growth and/or retention of the stem cells at the site of implantation. In addition, the scaffold may facilitate migration of endogenous cells into the administration site. The scaffold may be implanted or applied at the tissue defect site, followed by the administration of the pyruvate kinase protein. One example includes a method for facilitating tissue transplantation and cell transplantation contacting a site of transplantation with a protein substantially similar to pyruvate kinase M2. In some examples, the cells to be transplanted can be mixed with a protein substantially similar to pyruvate kinase.

The pyruvate kinase protein can be administered to a subject in need of such treatment alone or be co-administered with one or more other therapeutic agents. For example, the pyruvate kinase protein can be co-administered in combination with therapeutic agents conventionally used for promoting angiogenesis and/or wound healing. By "co-administered" is meant simultaneous administration in the same formulation or in two different formulations by the same or different routes, or sequential administration by the same or different routes, whereby the pyruvate kinase protein and other therapeutic agent(s) exhibit overlapping therapeutic windows. By "sequential" administration is meant one is administered after the other. Such further agents that may be co-administered with the pyruvate kinase protein include platelet-derived growth factor (PDGF), transforming growth factor-.beta. (TGF-β), platelet-derived wound healing factor, insulin growth factor (IGF), keratinocyte growth factor (KGF), anti-inflammatory agents and anti-microbial agents. Further examples of other therapeutic agents used for promoting angiogeneisis and/or wound healing that may be co-administered with the pyruvate kinase protein include indoleamine 2,3-dioxygenase (IDO), tryptophan dioxygenase (TDO), spingosine-1-phosphate (SIP), N-acylethanolamines, grapefruit extract and other plant phytochemicals including ascein, green tea catechins, melatonin, arginine and other amino acids for support of vessel growth.

The pyruvate kinase protein will generally be formulated into a pharmaceutical composition comprising the protein and a pharmaceutically acceptable carrier. Suitable pharmaceutical compositions include topically acceptable formulations such as creams, lotions, ointments and gels, and biodegradable gel or matrix for internal or external application. Topically acceptable compositions can be applied directly to the site of treatment including by way of dressings and the like impregnated with the preparation. Gels comprising a pyruvate kinase protein precipitate are particularly suitable. Gels and other pharmaceutical compositions as described herein may also include calcium ions and/or salts. The presence of calcium in the composition can enhance wound healing.

A pharmaceutical composition as described herein can also incorporate one or more preservatives such as parabens, chlorobutanol, and sorbic acid, binders such as corn starch or gelatin, thickening agents, emulsifiers, surfactants, gelling agents, and other components typically used in such compositions. Pharmaceutically acceptable carriers include any suitable conventionally known topically and physiologically acceptable solvents, dispersion media, isotonic preparations and solutions. Use of such ingredients and media for pharmaceutically active substances is well known. Except insofar as any conventional media or agent is incompatible with the pyruvate kinase protein, use thereof is expressly encompassed.

Pharmaceutical compositions embodied by the invention include therapeutic compositions for human or veterinary use. Typically, the pharmaceutical composition will have a pH suitable for application of the composition directly to a wound. Generally, the pH will be above 5 and usually, about 7 or higher. Pyruvate kinase protein precipitate gels as described herein can precipitated from a solution containing the protein and a physiologically acceptable buffer system such that the precipitate has the desired pH. Alternatively, the pH of the gel can be altered to the desired pH by the addition of any suitable pH modifier(s) to the gel.

A pharmaceutical composition embodied by the invention will generally contain at least about 0.001% by weight of the pyruvate kinase protein up to about 80% w/w of the composition. For example, the pharmaceutical composition can contain about 0.05%, 0.01%, 0.1%, 1%, 10%, 20%, 30%, 40%, 50%, 60%, 70%, or 80% by weight of the pyruvate kinase protein or substantially similar protein. The amount of the protein in the composition will be such that a suitable effective dosage will be delivered to the subject taking into account the proposed mode of administration.

The dosage of the pyruvate kinase protein administered in accordance with an embodiment of the invention will depend on a number of factors including whether the protein is to be administered for prophylactic or therapeutic use, the disease or condition for which the protein is intended to be administered, the severity of the condition, the sex and age of the subject, and related factors including weight and general health of the subject, and can be determined in accordance with accepted medical principles. For instance, a low dosage can initially be given which is subsequently increased at each administration following evaluation of the subject's response. Similarly, the frequency of administration can be determined in the same way that is, by continuously monitoring the subject's response between each dosage and if desirable, increasing the frequency of administration or alternatively, reducing the frequency of administration.

Typically, the pyruvate kinase protein will be administered in accordance with a method embodiied by this disclosure. For topical application, the pyruvate kinase protein will be administered to a tissue or wound site by covering the site with the pharmaceutical composition containing 0.5%-0.01% by weight PKM2

Routes of administration include but are not limited to topically, respiratorialy, intravenously, orally, intraperitonealy, subcutaneously, intramuscularly, rectally, topically and by implant. With respect to intravenous routes, particularly suitable routes are via injection into blood vessels which supply the target tissue to be treated. The pyruvate kinase protein can also be delivered into cavities such for example the pleural or peritoneal cavity, cranial or be injected directly into the tissues to be treated. For oral administration, the pyruvate kinase protein can be encapsulated or otherwise provided in an enteric for passage through the stomach and release in the small intestine. Any suitable such enteric formulation or coating can be utilized.

Moreover, a pyruvate kinase protein can also be coated onto the surface of a stent or balloon of a catheter such as an angioplasty catheter, or other surgical instrument for application to the interior wall of a blood vessel during angioplasty or other surgical procedure. The pyruvate kinase can for instance be applied to the wall of the blood vessel in this manner in the form of a gel or any other appropriate formulation to promote wound healing and/or angiogenesis or epithelial cell migration to the site of treatment.

Suitable pharmaceutically acceptable carriers and formulations useful in compositions embodied by the invention can for instance be found in handbooks and texts.

EXAMPLES

Example 1

The following is an exemplary pyruvate kinase M2 sequence.

(SEQ ID NO: 1)
PKM2 Accession No. NP 002645
```
  1 mskphseagt afiqtqqlha amadtflehm crldidsppi tarntgiict igpasrsvet 61 lkemiksgmn varlnfshgt heyhaetikn vrtatesfas dpilyrpvav aldtkgpeir 121 tglikgsgta evelkkgatl kitldnayme kcdenilwld yknickvvev gskiyvddgl 181 islqvkqkga dflvteveng gslgskkgvn lpgaavdlpa vsekdiqdlk fgveqdvdmv
```

-continued

```
241 fasfirkasd vhevrkvlge kgknikiisk ienhegvrrf deileasdgi mvargdlgie 301 ipaekvflaq kmmigrcnra gkpvicatqm lesmikkprp traegsdvan avldgadcim 361 lsgetakgdy pleavrmqhl iareaeaaiy hlqlfeelrr lapitsdpte atavgaveas 421 fkccsgaiiv ltksgrsahq varyrprapi iavtrnpqta rgahlyrgif pvlckdpvqe 481 awaedvdlrv nfamnvgkar gffkkgdvvi vltgwrpgsg ftntmrvvpv p
```

Example 2

Figure 1A:
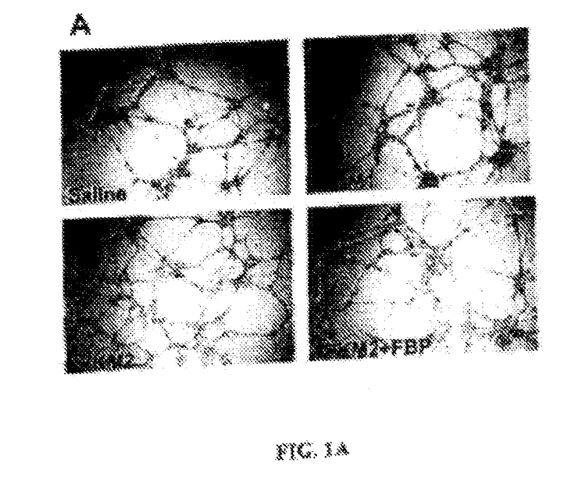
FIG. 1A shows graphically that endothelial HUVEC cells treated with a pyruvate kinase M2 had increased formation of endothelial tubes, more branch points, and longer tubes compared with the cells treated with controls.
Figure 1B:
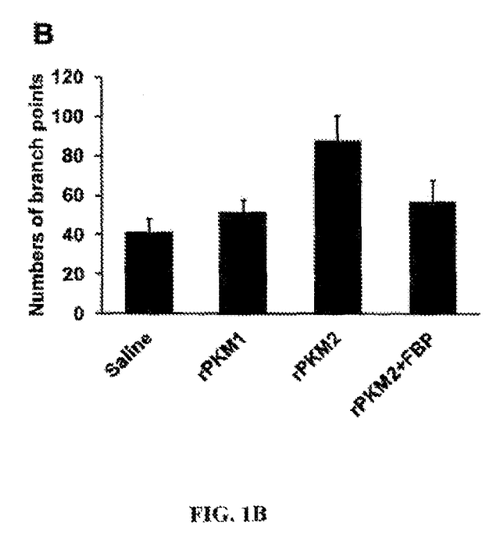
FIG. 1B shows graphically endothelial cells treated with a pyruvate kinase M2 had increased branch points in the tube formation assays compared with cells treated with controls.

In vitro tests supported that PKM2 promoted angiogenesis. PKM2 expressed as recombinant PKM2 (ref to as rPKM2) and its isoenzyme PKM1 (ref to as rPKM1) as a control. The rPKM2, the rPKM2+ fructose bisphosphate (FBP), the rPKM1, and a buffered solution alone were added to the culture medium of the cells. Formation of the endothelial tubes was analyzed. As shown in FIG. 1A and FIG. 1B, rPKM2 strongly promoted endothelial tube formation both in tube density and the sprouts of the formed tubes. The time required for formation of the tubes was also substantially shortened, and the formed tubes were maintained much longer time. The rPKM2+FBP had less effects compared to that of the rPKM2. The rPKM1 had only marginal effects, while buffered saline had no effects.

Example 3

Figure 2:
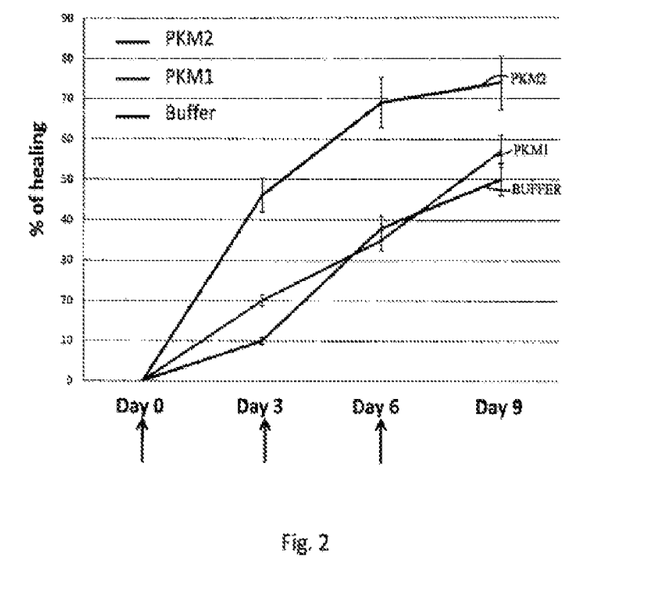
FIG. 2 shows that the area of wounds treated with a pyruvate kinase M2 protein reduces more effectively and had earlier granulation formation compared with wounds treated with controls.
Figure 3A:
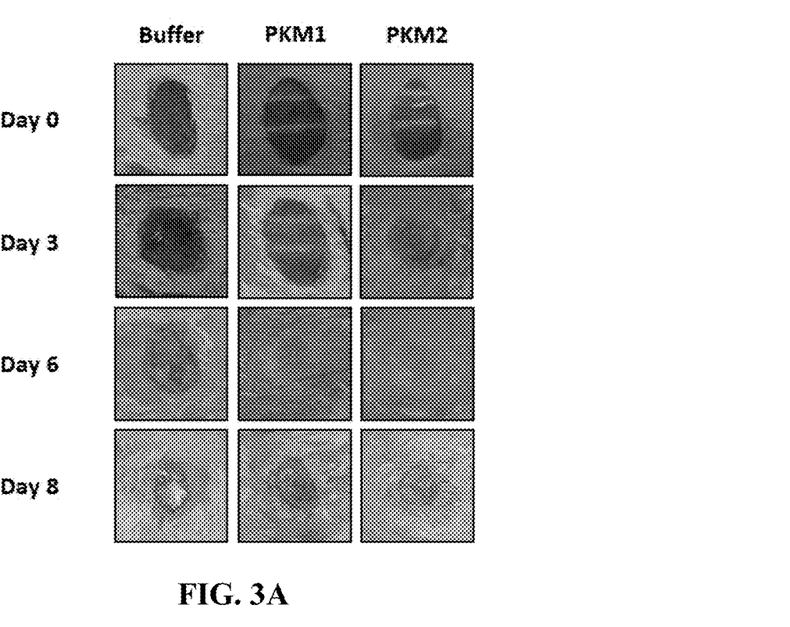
FIG. 3A shows graphically that the wound treated with a pyruvate kinase M2 protein reduces more effectively compared with words treated with controls.
Figure 3B:
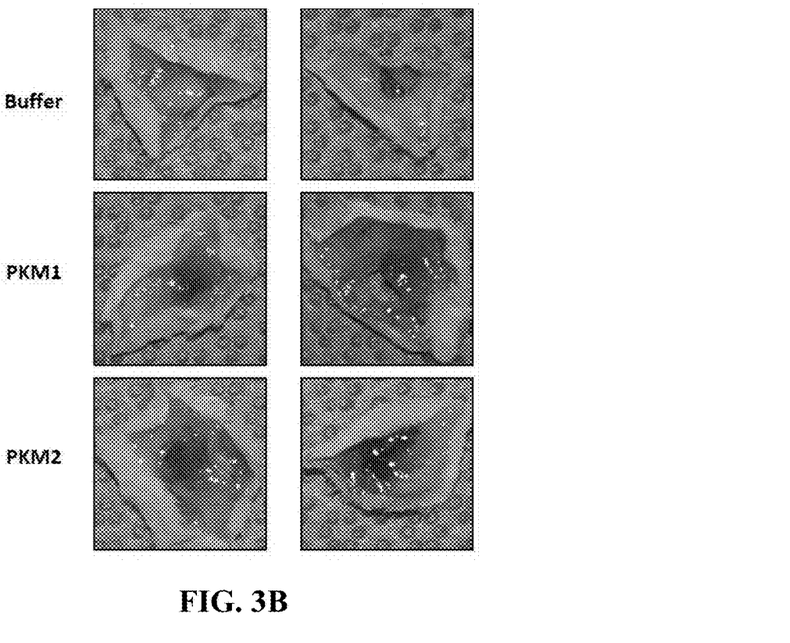
FIG. 3B shows graphically (from inside the wound) that the wound areas treated with a pyruvate kinase M2 protein reduces more effectively compared with wounds treated with controls.
Figure 4:
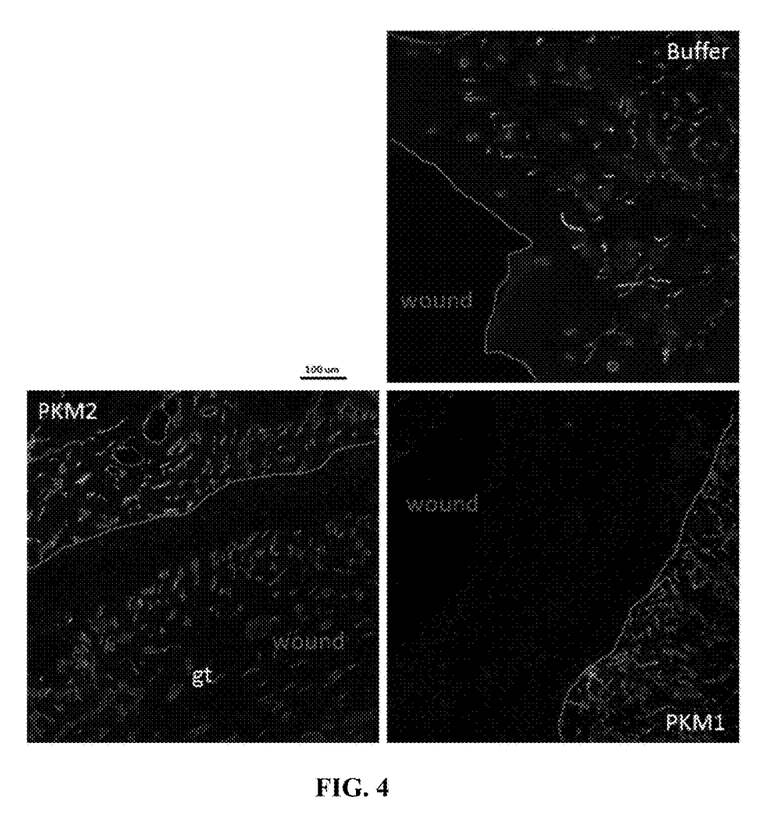
FIG. 4 shows that wounds treated with a pyruvate kinase M2 protein have increased angiogenesis compared with wounds treated with controls.

In vivo tests supported that PKM2 promoted wound healing by facilitating angiogenesis. A wound was induced in mice. A cream without PKM2 was administered on the wound to a sample of the mice, and a cream with PKM2 was administered on the wound to another sample of the mice. The wounds were then covered and dressed. The topical applications of the agents were applied again three days and six days after wound inductions. The experiments were stopped at nine days. After 3 days, there was a difference in wound healing and closure. FIGS. 2 through 4 show this data.

Example 4

The following are the amino acid sequences of modified pyruvate kinase proteins in which at least arginine has been substituted with a glutamate.

(SEQ ID NO: 2)
```
R399E Mutant
  1 mskphseagt afiqtqqlha amadtflehm crldidsppi tarntgiict igpasrsvet 61 lkemiksgmn varlnfshgt heyhaetikn vrtatesfas dpilyrpvav aldtkgpeir 121 tglikgsgta evelkkgatl kitldnayme kcdenilwld yknickvvev gskiyvddgl 181 islqvkqkga dflvteveng gslgskkgvn lpgaavdlpa vsekdiqdlk fgveqdvdmv 241 fasfirkasd vhevrkvlge kgknikiisk ienhegvrrf deileasdgi mvargdlgie 301 ipaekvflaq kmmigrcnra gkpvicatqm lesmikkprp traegsdvan avldgadcim 361 lsgetakgdy pleavrmqhl iareaeaaiy hlqlfeeler lapitsdpte atavgaveas 421 fkccsgaiiv ltksgrsahq varyrprapi iavtrnpqta rgahlyrgif pvlckdpvqe 481 awaedvdlrv nfamnvgkar gffkkgdvvi vltgwrpgsg ftntmrvvpv p
```

(SEQ ID NO: 3)
```
Y105E Mutant
  1 mskphseagt afiqtqqlha amadtflehm crldidsppi tarntgiict igpasrsvet 61 lkemiksgmn varlnfshgt heyhaetikn vrtatesfas dpilerpvav aldtkgpeir 121 tglikgsgta evelkkgatl kitldnayme kcdenilwld yknickvvev gskiyvddgl 181 islqvkqkga dflvteveng gslgskkgvn lpgaavdlpa vsekdiqdlk fgveqdvdmv 241 fasfirkasd vhevrkvlge kgknikiisk ienhegvrrf deileasdgi mvargdlgie 301 ipaekvflaq kmmigrcnra gkpvicatqm lesmikkprp traegsdvan avldgadcim 361 lsgetakgdy pleavrmqhl iareaeaaiy hlqlfeelrr lapitsdpte atavgaveas 421 fkccsgaiiv ltksgrsahq varyrprapi iavtrnpqta rqahlyrgif pvlckdpvqe 481 awaedvdlrv nfamnvgkar gffkkgdvvi vltgwrpgsg ftntmrvvpv p
```

Example 5

Figure 5A:
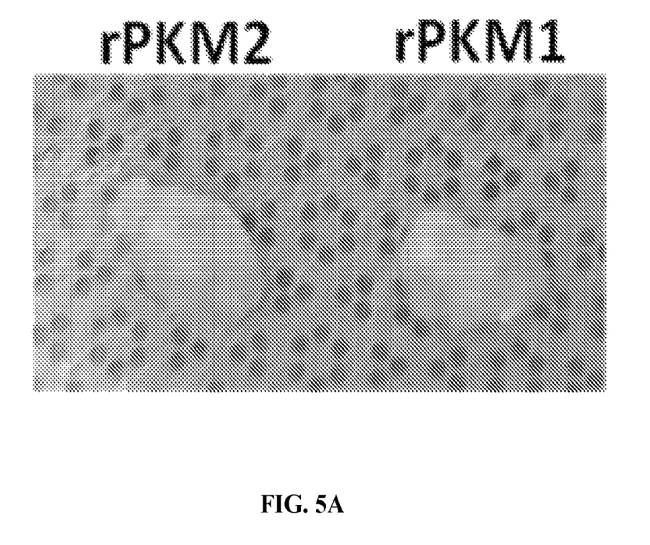
FIG. 5A shows a representative pictures of the retrieved matrix-gel plaques.

A gel plaque assay, a matrix-gel having rPKM2 (3 mM) or rPKM1 (3 mM), respectively, was implanted into the right flank of Balb/c mice. The matrix-gel was pre-mixed with other materials suggested by vendor before addition of rPKM1 and rPKM2 gels. After seven days, the matrix-gel plagues were retrieved from mouse. FIG. 5A shows a representative pictures of the retrieved matrix-gel plaques.

Figure 5B:
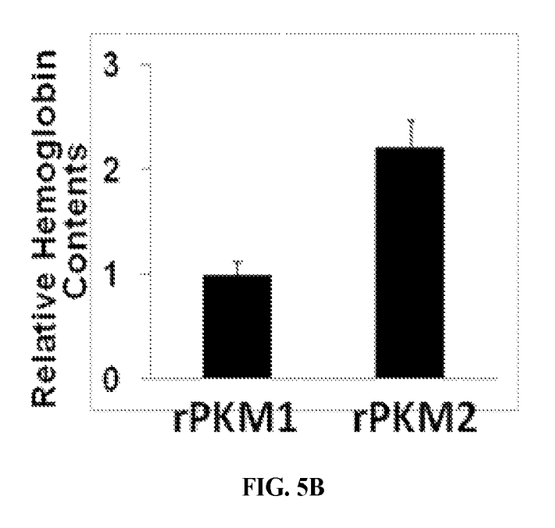
FIG. 5B shows that the hemoglobin contents in the matrix-gel plaques having PKM2 gel and rPKM1 gel.

FIG. 5B shows that the hemoglobin contents in the matrix-gel plaques having PKM2 gel was larger relative to the hemoglobin content in the matrix-gel plaques having rPKM1 gel. The assay indicates the activity of rPKM2 in promoting angiogenesis.

Example 6

Figure 6:
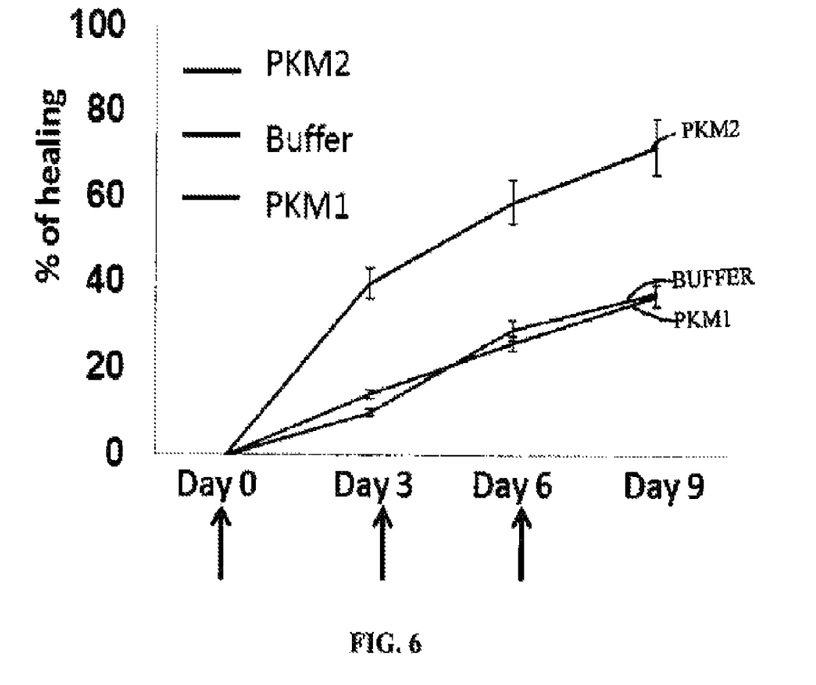
FIG. 6 shows that wounds treated with pyruvate kinase M2 protein show significantly greater healing percentages than those treated with controls.

In vivo tests supported that PKM2 promoted wound healing by facilitating angiogenesis with diabetic db/db mice. A wound was induced in mice. A cream without PKM2 was administered on the wound to a group of the mice, and a cream with PKM2 was administered on the wound to another sample of the mice. The wounds were then covered and dressed. FIG. 6 shows a wound that was induced in diabetic db/db mice (13 weeks old, six mice per group). A cream without PKM2 was topically administered on the wound, and a cream with PKM2/Buffer (0.004% w/w) was topically administered on the wound, and a cream with PKM1 (0.004% w/w)(Blue) was topically administered on the wound. The degree or percentage of healing was plainly higher in mice where PKM2 was applied thereto. The percent (%) of healing was determined by measuring the initial wound areas and then subtracting measured wound areas at a given day/initial wound areas. The error bars are the standard deviations among the five mice.

The invention claimed is:

1. A method for stimulating angiogenesis or blood vessel growth in tissue of a subject in need of angiogenesis stimulation or blood vessel growth, the method comprising administering to the subject a therapeutically effective dose of a protein having at least 70% sequence identity to wild-type pyruvate kinase M2 (PKM2) of SEQ ID NO: 1 by contacting the tissue with said protein, wherein the protein is in dimeric form.

2. The method as claimed in claim 1, wherein the has a mutation selected from the group consisting of: R388E and Y105E of SEQ ID NO: 1.

3. The method as claimed in claim 1, wherein the protein is wild-type pyruvate kinase M2 from a human (SEQ ID NO: 1), and is in dimeric form and has angiogenesis stimulating activity.

4. The method as claimed of claim 3, wherein the protein is in a pharmaceutically acceptable carrier.

5. The method as claimed in claim 1, wherein the tissue is contacted topically with the protein through a topical formulation containing the protein.

6. A method of promoting endothelial cell migration in a tissue of a mammal in need of endothelial cell migration comprising contacting the tissue with an endothelial cell migration-stimulating amount of a wild-type pyruvate Kinase type M2, wherein the protein is in dimeric form.

7. A method of treating skin injuries in a subject in need thereof by administering to the subject a pharmaceutical composition comprising a protein having at least 70% sequence identity to wild-type pyruvate kinase M2 (PKM2) of SEQ ID NO: 1, wherein the protein is in dimeric form.

8. A method for facilitating tissue transplantation and cell transplantation comprising the steps of: contacting a site of transplantation with a protein having at least 70% sequence identity to wild-type pyruvate kinase M2 of SEQ ID NO: 1, wherein the protein is in dimeric form.

9. The method of claim 8, further comprising the step of: providing cells mixed with the protein, wherein the cells are stem cells.

10. A method of increasing angiogenesis in a cell, group of cells, or organism all in need thereof, comprising administering a pharmaceutically acceptable composition comprising a protein having at least 70% sequence identity to wild-type pyruvate kinase M2 (PKM2) of SEQ ID NO: 1 to the cell, group of cells, or organism in need of increased angiogenesis, wherein the pharmaceutical composition increases angiogenesis and causes a change in the cell, the group of cells, or the organism; and the protein is in dimeric form.

11. The method of claim 10, wherein the organism has an angiogenesis-related disorder of macular degeneration, corneal ulceration, stroke, ischemic heart disease, infertility, ulcers, scleroderma, wound healing, ischemia, ischemic heart disease, myocardial infarction, myocardosis, angina pectoris, and unstable angina.

12. The method of claim 10, wherein the cells or group of cells is used in scaffolding, skin transportation, and tissue engineering.

13. The method of claim 1, wherein the contact is extracellular contact.

* * * * *